United States Patent
Khan et al.

(10) Patent No.: US 12,318,449 B2
(45) Date of Patent: *Jun. 3, 2025

(54) COMBINATION THERAPY USING RILUZOLE TO ENHANCE TUMOR SENSITIVITY TO IONIZING RADIATION

(71) Applicant: Rutgers, The State University of New Jersey, New Brunswick, NJ (US)

(72) Inventors: Atif J. Khan, Monroe, NJ (US); Suzie Chen, Highland Park, NJ (US); James S. Goydos, East Brunswick, NJ (US); Bruce G. Haffty, Somerset, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/489,642

(22) Filed: Oct. 18, 2023

(65) Prior Publication Data
US 2024/0042033 A1  Feb. 8, 2024

Related U.S. Application Data

(63) Continuation of application No. 17/545,559, filed on Dec. 8, 2021, now Pat. No. 11,813,331, which is a continuation of application No. 16/953,559, filed on Nov. 20, 2020, now Pat. No. 11,229,704, which is a continuation of application No. 13/768,544, filed on Feb. 15, 2013, now Pat. No. 10,864,271.

(60) Provisional application No. 61/599,233, filed on Feb. 15, 2012.

(51) Int. Cl.
*A61K 41/00* (2020.01)
(52) U.S. Cl.
CPC .................. *A61K 41/0038* (2013.01)
(58) Field of Classification Search
CPC .................................................. A61K 41/0038
See application file for complete search history.

(56) References Cited

U.S. PATENT DOCUMENTS

| | | | |
|---|---|---|---|
| 5,869,609 A * | 2/1999 | Mulvihill | C07K 14/70571 536/23.5 |
| 6,589,991 B1 * | 7/2003 | Lai | A61K 31/5377 514/599 |
| 6,589,998 B1 * | 7/2003 | Bianchi | A61B 17/54 424/9.1 |
| 6,797,692 B1 * | 9/2004 | Ikonomidou | A61K 45/06 514/17.4 |
| 6,923,966 B2 * | 8/2005 | Rybak | A61K 38/212 424/85.4 |
| 6,998,391 B2 * | 2/2006 | Lyons | A61P 37/00 424/45 |
| 7,129,073 B2 * | 10/2006 | Liu | A61P 43/00 435/194 |
| 7,385,103 B2 * | 6/2008 | Chen | C12N 15/8509 800/13 |
| 7,456,267 B2 * | 11/2008 | Elson | A61K 38/212 536/20 |
| 7,691,377 B2 * | 4/2010 | Goydos | A61K 31/27 514/367 |
| 10,864,271 B2 * | 12/2020 | Khan | A61K 41/0038 |
| 2001/0046491 A1 | 11/2001 | Valerie | |
| 2005/0235366 A1 | 10/2005 | Chen | |
| 2008/0124333 A1 | 5/2008 | Goydos et al. | |
| 2010/0221246 A1 | 9/2010 | Goydos et al. | |

FOREIGN PATENT DOCUMENTS

WO  2010138377 A1  12/2010

OTHER PUBLICATIONS

Atallah et al: "Treatment of metastatic malignant melanoma.", Current Treatment Options in Oncology, May 2005, vol. 6, No. 3, May 2005 (May 2005), pp. 185-193.
Eisen et al: "Sorafenib in advanced melanoma: a Phase II randomised discontinuation trial analysis", British Journal of Cancer, vol. 95, No. 5, Sep. 2006 (Sep. 2006), pp. 581-586.
Green et al: "Effects fo ruluzole (RZ) and ionizing raditiaon (IR) in metabotropic glutamate receptor-1 (GRM1) positive human melanoma," ASCO Ann Mtg proc, 2009, vol. 27, No. 15S, abs. 9083.
Haas et al: "The non-competitive metabotropic glutamate receptor-1 antagonist CPCCOEt inhibits the in vitro growth of human melanoma", Oncology Reports, vol. 17, No. 6, Jun. 2007, pp. 1399-1404.
Khan et al: "The glutamate release inhibitor riluzole increases DNA damage and enhances cytotoxicity in human glioma cells, in vitro and in vivo", Oncotarget, 2019, 10(29), pp. 2824-2834.
Koukourakis et al: Temozolomide with Radiation Therapy in High Grade Brain Gliomas: Pharmaceuticals Considerations and Efficacy; A Review Article; Molecules 2009, vol. 14, pp. 1561-1577.
Mantz, Jean: "Riluzole," CNS Drug Reviews, 1996, vol. 2, No. 1, pp. 40-51.
Namkoong et al: "Metabotropic Glutamate Receptor 1 and Glutamate Signaling in Human Melanoma", Cancer Research, Mar. 2007, vol. 67, No. 5, pp. 2298-2305.
National Cancer Institute, Definition of Antogonist, electronic resource, [http://www.cancer.gov/disctionary/?print=1&cdrid=350250], retrieved on Oct. 28, 2012.
Rzeski et al: "Glutamate antagonists limit tumor growth," PNAS, May 22, 2001, vol. 98, No. 11, pp. 6372-6377.
Stupp et al: "Effects of Radiotherapy with Concomitant and Adjuvant Temozolomide Versus Radiotherapy Alone on Survival in Glioblastoma in a Randomised Phase III Study: 5-Year Analysis of the EORTC-NCIC Trial", Lancet Oncology, May 2009, vol. 10, pp. 458-466.

(Continued)

*Primary Examiner* — Sikarl A Witherspoon
(74) *Attorney, Agent, or Firm* — FOX ROTHSCHILD LLP

(57) ABSTRACT

Disclosed is a method of treating a tumor in a patient, comprising (a) administering riluzole in an amount effective to sensitize the tumor cells to ionizing radiation, and (b) irradiating the tumor cells with ionizing radiation in a dose effective to reduce tumor cell growth. The method can further comprise administering an effective amount of one or more additional therapeutic agents.

25 Claims, 4 Drawing Sheets

(56) References Cited

OTHER PUBLICATIONS

Wall et al: "Riluzole is a radio-sensitizing agent in an in vivo model of braid metastatis dervived from GRM1 expressing human melanoma cells", Pigment Cell Melanoma Res., 2015, 28(1), pp. 105-109.
Yao et al: "Enhancement of glutamate uptake mediates the neuroprotection exerted by activating group II or III metabotropic glutamate receptors on astrocytes", Journal of Neurochemistry, 2005, vol. 92, pp. 948-961.
Zhang et al: "Sensitization of C6 glioma cells to radiation by staurosporine, a potent protein kinase C inhibitor", Journal of Neuro-Oncology, 1993, vol. 15, pp. 1-7.

* cited by examiner

COMBINATION THERAPY USING RILUZOLE TO ENHANCE TUMOR SENSITIVITY TO IONIZING RADIATION

CROSS-REFERENCE TO RELATED APPLICATIONS

The present application is a continuation of U.S. patent application Ser. No. 17/545,559, filed Dec. 8, 2021, which is a continuation of U.S. patent application Ser. No. 16/953,559, filed Nov. 20, 2020, now U.S. Pat. No. 11,229,704, which is a continuation of U.S. patent application Ser. No. 13/768,544, filed Feb. 15, 2013, now U.S. Pat. No. 10,864,271, which in turn claims the benefit of priority under 35 U.S.C. § 119(e) of U.S. Provisional Application No. 61/599,233, filed Feb. 15, 2012. The entire disclosures of which are incorporated herein by reference in their entireties.

STATEMENT REGARDING FEDERALLY SPONSORED RESEARCH OR DEVELOPMENT

This invention was made with government support under Contracts No. RO1CA73077 and RO1CA124975 awarded by the National Institutes of Health. The government has certain rights in the invention.

BACKGROUND OF THE INVENTION

Few therapeutic options exist for patients with brain metastases. A well-tolerated oral agent with CNS penetration that enhances the effects of whole brain irradiation would be of significant value. Brain metastases represent a common terminal or preterminal event in many patients with malignancy including a large proportion of patients with metastatic melanoma. Current therapy for patients with brain metastases involves some combination of steroids, surgical resection, stereotactic radiosurgery, and whole brain radiation therapy (WBRT). Most patients with brain metastases will receive WBRT as one component of their therapy. Available evidence suggests that the histology of brain metastases is prognostically relevant. Melanoma patients with brain metastases who receive WBRT have inferior outcomes when compared with other cancer types. This clinical finding supports the known relative radioresistance of melanoma cell lines in vitro. To date, efforts at combining systemic agents with WBRT to enhance the lethal effects of radiotherapy in melanoma patients have had limited success.

In contrast to most tumor cell types, significant evidence exists that at least some melanoma cell lines have high capacity for repair of sublethal DNA damage caused by ionizing radiation. In an attempt to address the perceived radioresistance of melanoma, many investigators have adopted radiotherapy schedules that deliver larger daily fractions of radiation (hypofractionation) to exploit the sensitivity of these cells to larger fraction sizes. However, these large daily fractions cannot be delivered to the whole brain for patients with brain metastases due to the risk of late neurotoxicity.

Melanoma is the fourth most common cause of brain metastases. It also has one of the highest rates of brain metastases; up to 50% of patients dying of melanoma have brain metastases. The median survival of melanoma patients with brain metastases treated with WBRT ranges between 3 and 5 months. In a report by Fife and colleagues on 686 patients with metastatic melanoma to brain, 205 patients treated with resection with or without WBRT had a median survival of 9 months, 236 patients treated with WBRT had a median survival of 3.4 months, and patients treated with supportive care alone had a median survival of 2 months (Fife K M, et al., Determinants of outcome in melanoma patients with cerebral metastases. J. Clin. Oncol. 2004; 22: 1293-1300).

Similarly, high-grade gliomas are particularly vexing tumors that indiscriminately devastate both adults and children alike. The addition of concurrent and post-concurrent temozolamide to radiation therapy (RT) has provided an advance in glioblastoma therapy. Still, the overall prognosis remains decidedly poor, even in patients with methyl-silenced $O^6$-methylguanine-DNA methyl-transferase (MGMT) expression.

BRIEF SUMMARY OF THE INVENTION

The concept of targeting glutamatergic signaling in order to enhance radiation sensitivity is unknown in the prior art, and is a significant paradigm shift from current strategies in glioma and metastatic disease therapies. It has now been discovered that by targeting the glutamate signaling pathway of such tumors utilizing the well-tolerated FDA-approved drug riluzole (RIL), which crosses the blood brain barrier and has been used for years in patients with amyotrophic lateral sclerosis (ALS), the sensitivity of blastomas and metastatic melanomas to ionizing radiation is enhanced.

One embodiment of the present invention is directed to a method of treating a tumor in a patient, where the tumor comprises cells expressing a metabotropic glutamate receptor, the method comprising: (a) administering riluzole in an amount effective to sensitize the tumor cells to ionizing radiation, and (b) irradiating the tumor cells with ionizing radiation in a dose effective to reduce tumor cell growth. The tumor can be a glioma, a melanoma, a metastatic melanoma, or other metastatic tumor. The metastatic tumor, including metastatic melanoma, can be to the brain. The tumor and its associated tumor cells preferably express metabotropic glutamate receptor 3 (mGluR3; GRM3) for a glioma, and metabotropic glutamate receptor 1 (mGluR1; GRM1) for melanoma or metastatic melanoma. In one particular embodiment of the method, the tumor is a brain tumor, for example a glioma or a metastatic melanoma. The method can also further comprise administering one or more additional therapeutic agents in an amount effective to kill the tumor cells when used in combination with riluzole and ionizing radiation.

The amount of riluzole administered is generally in the range used for the treatment of ALS (Lou Gehrig's disease), preferably about 50 to about 200 mg/day. Riluzole treatment can begin up to 48 hours prior to radiation treatment, can continue up to or even during radiation treatment, and can also continue post-radiation treatment at the same or a lower dosage.

The dose of ionizing radiation administered in the combination treatment is preferably from about 200 to 6000 cGy/day, and more preferably about 250 to about 3750 cGy/day. For brain tumors the ionizing radiation can comprise whole-brain irradiation or fractionated whole-brain irradiation.

DETAILED DESCRIPTION OF THE INVENTION

Figure 1A:
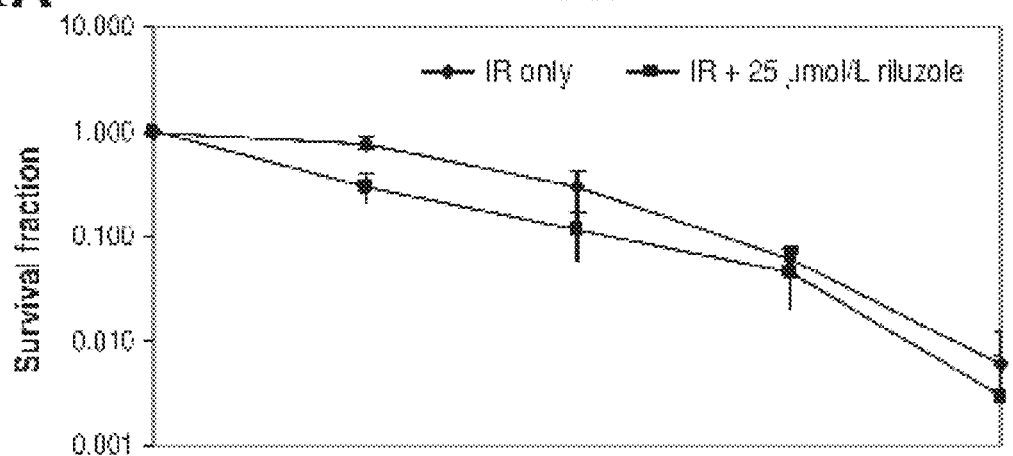
FIG. 1A shows survival fraction of hGRM1-positive C8161 human melanoma cells treated with riluzole at 25 mmol/L for 24 hours, followed by escalating doses of ionizing radiation (IR).

Riluzole (RIL) is an FDA-approved drug for the treatment of amyotrophic lateral sclerosis and has off-label uses in other psychiatric and neurologic disorders. Riluzole possesses both glutamatergic-modulating and neuroprotective properties. A recent phase 0 trial of riluzole in patients with stage III and stage IV melanoma, demonstrated that approximately one third of the patients exhibited remarkable clinical and metabolic responses. Comparisons by biochemical markers between pre- and post-treatment samples showed suppression of components of two of the major signaling pathways important in melanoma pathogenesis, MAPK and PI3K/AKT, and an increase in the number of apoptotic cells in post treatment tumor samples.

Treatment of melanoma cells with riluzole results in synchronization of the cells in G2/M, followed soon thereafter by a spike in the sub-G1 population indicating apoptosis. Cells in G2/M are exquisitely sensitive to DNA damaging agents such as ionizing radiation. Further, it has now been discovered that riluzole serves as a radiation sensitizer for the treatment of metastatic melanoma. Since riluzole also crosses the blood brain barrier, it is of particular clinical relevance because brain metastases are commonly treated with whole brain radiation therapy (WBRT).

High-grade gliomas also have aberrant glutamate signaling. Glioma cells invade local tissues by inducing excitotoxic cell death in surrounding neurons mediated by reduced uptake of glutamate by the EAAT1/2 receptors and increased release of glutamate mediated by the $X^c$ system. Prolonged synaptic activation from excess glutamate can lead to "excitotoxic" cell death, and is now known to be a final common death pathway in many neurological injuries. The excitatory amino acid transporters 1 and 2 (EATT1 and 2) are $Na^{2+}$ dependent glutamate transporters expressed on normal astrocytes that maintain extracellular glutamate levels at µM concentrations. Glioma cells lack expression of EATT2 and appear to have EATT1 mislocalized to the nucleus, resulting in no functional glutamate uptake. It has been demonstrated that lower levels of EATT2 are expressed in high-grade gliomas and no detectable EATT2 is expressed in glioblastomas. At the interface of glioma and normal brain, IHC analysis has demonstrated low EATT2 levels on the tumor side and prominent expression of EATT2 in astrocytes in uninvolved brain. Paradoxically, glioma cells release glutamate through system $X^c$, a glutamate-cystine antiporter system composed of two proteins, xCT and CD98. xCT levels are elevated in gliomas; xCT ablation by siRNA results in massive reduction in glutamate secretion, and conditioned media from glioma cells results in neuronal degeneration only if xCT is functional. Thus, decreased uptake and excess secretion of extracellular glutamate in the microenvironment facilitates intracranial glioma progression and expansion.

Extracellular glutamate acts as a trophic factor that activates proliferative intracellular signals, and as a pro-motility factor that enhances cell migration. It has been demonstrated that glioma-initiating CD133-positive stem cells express the metabotropic glutamate receptor 3 (GRM3 or mGluR3), that pharmacologic blockade of mGlu3 results in committed differentiation into benign astrocyte-like cells, that activation of mGlu3 inhibits bone-morphogenetic protein receptor induced differentiation by activating the MAPK pathway, and that treatment with an mGlu3 receptor antagonist suppressed in vivo tumor growth in a mouse intracranial glioblastoma model of implanted CD133+ stem cells (or "tumor-initiating cells"). Moreover, mGluR3 is consistently found in human glioblastomas and may be a primary mediator of glutamate-induced trophic signaling through the MAPK and PI3 pathways. Stimulation of mGluR3 downregulates EATT transports, thus exacerbating glutamate excitotoxicity and glioma progression, while pharmacologic blockade of mGluR3 inhibits glioma growth.

Upregulation of the $X^c$ system allows gliomas to enhance uptake of cystine which leads to increased synthesis of the cellular antioxidant glutathione (GSH), thus conferring resistance to oxidative stresses such as radiation therapy (RT). As already described, gliomas commonly have upregulated levels of the $X^c$ that exchanges intracellular glutamate with extracellular cystine. Cystine transport and supply is the rate-limiting step for cellular production of GSH, a tripeptide of glutamate, cysteine (reduced cystine), and glycine. GSH is an important intracellular antioxidant that protects cells against damage from endogenous reactive oxygen species (ROS), and elevated GSH levels have been shown to confer radioresistance. Pharmacologic inhibitors of system $X^c$ can completely deplete glioma cells of GSH with resulting tumor suppression. This growth arrest can be reversed by rescue with a membrane-permeant GSH ester. Radiation-induced cell kill is highly dependent on ROS.

Riluzole is an FDA-approved drug with excellent CNS penetration and minimal toxicity used for the treatment of amyotrophic lateral sclerosis (ALS) and other off-label uses. Riluzole possesses both glutamatergic modulating and neuroprotective properties mediated by ionotropic and metabotropic glutamate receptors. Riluzole inhibits the release of glutamate, behaving as a non-competitive inhibitor of glutamate receptors, and activates EATT transporters. Specifically, riluzole has been shown to upregulate GLT-1/EATT2 receptors thus normalizing glutamate exchange in glial cells, which is highly relevant given the above discussion of glioma pathogenesis. Riluzole tends to normalize glutamate homeostasis non-specifically and thus has activity at multiple glutamergic targets. The doses of RIL used in the in-vitro and in-vivo cancer models fall in the range of doses clinically used in the treatment of ALS. Furthermore, riluzole has been shown to protect normal brain from the effects of ionizing radiation in animal models. It has also been demonstrated that glutamate blockade reduces excitotoxicity and glioma-associated seizure activity in mice. Although not wishing to be bound by any theory, it is believed that overexpression of system $X^c$ increases intracellular glutathione and increases extracellular glutamate which then acts as a paracrine/autocrine trophic factor for glioma progression through stimulation of mGluR3.

The concept of targeting glutamate signaling as a therapeutic strategy in glioblastoma is a significant paradigm shift from current clinical treatment strategies. RIL is a well-tolerated oral agent that has been used chronically for decades for the treatment of ALS, and has CNS penetration. The concept of using MR (Magnetic Resonance) spectroscopy to measure peri-tumoral glutamate levels is unknown in the prior art, and allows non-invasive measurement of intracranial drug effects. Further, using primary glioblastoma samples, a novel zebrafish model of glioblastoma has been established that allows the testing of candidate combination therapies for efficacy with RT for clinical investigation.

One embodiment of the present invention is directed to a method of treating a tumor in a patient, the tumor comprising cells expressing a metabotropic glutamate receptor, the method comprising:
(a) administering riluzole in an amount effective to sensitize the tumor cells to ionizing radiation, and (b) irradiating the tumor cells with ionizing radiation in a dose effective to reduce tumor cell growth. The tumor can be a glioma, a melanoma, a metastatic melanoma, or other metastatic tumor. In a specific embodiment, the metastatic tumor is to the brain. The tumor and its associated tumor cells preferably express metabotropic glutamate receptor 3 (mGluR3; GRM3) for a glioma, and metabotropic glutamate receptor 1 (mGluR1; GRM1) for melanoma or metastatic melanoma. In one particular embodiment of the method, the tumor is a brain tumor, which can be for example, without limitation, a glioma or a metastatic melanoma. In one embodiment, the ionizing radiation comprises whole brain irradiation. In another embodiment, the ionizing radiation comprises fractionated whole brain irradiation or stereotactic irradiation. The method can also further comprise administering one or more additional therapeutic agents in an amount effective to kill the tumor cells when used in combination with riluzole and ionizing radiation. These additional therapeutic agents can include for example, and without limitation, the various classes of anticancer chemotherapeutic agents, especially those that cross the blood-brain barrier.

The dose of riluzole is generally in the range used for the treatment of ALS (Lou Gehrig's disease), preferably about 50 to about 200 mg/day, which may be administered in multiple smaller doses, including BID, or twice daily, or in a larger number of smaller doses as appropriate. In the case where the tumor cells are highly sensitized to radiation by the riluzole treatment, the amount of irradiation and/or section irradiated can be reduced. Riluzole and ionizing radiation can be dosed concurrently or sequentially; preferably, both are dosed concurrently. Further, riluzole pretreatment can begin up to 48 hours prior to radiation treatment, preferably 36-48 hours, and/or can continue post-concurrent phase at the same or a lower dose for maintenance for a variable period of time.

The dose of ionizing radiation is preferably from about 200-300 cGy daily to about 3000-6000 cGy, and more preferably about 200-300 cGy daily to about 3000-5000 cGy for metastatic disease to the brain. For brain tumors, the ionizing radiation can comprise whole-brain irradiation or fractionated whole-brain irradiation. A total radiation dose of about 3000-6000 cGy can be delivered in various fractionation schemes, to volumes that may encompass a part of, or the entire brain, over one or more phases of treatment.

A therapeutically "effective dose" is readily determined by those skilled in the art. With respect to riluzole, the effective dose encompasses the range normally used for the treatment of ALS and related disorders. Preferably the dose of riluzole is about 50-200 mg/day (Table 1), and may be given in a unitary dose or divided into several doses administered over the course of a 24-hour period. In one embodiment, riluzole is dosed twice daily (BID) throughout radiation, preferably at 100 mg per dose, to give a total dose of 200 mg/day. The mean half life of riluzole in vivo is 12 hours.

In the xenograft models, it has now been demonstrated, as detailed below, that the combination of riluzole and ionizing radiation results in an increase in the number of apoptotic cells in the tumors as compared with untreated controls or xenografts treated with either treatment alone. Furthermore, it has been shown that the combination of riluzole and ionizing radiation leads to a significant decrease in tumor growth compared with controls or either agent alone. It has also been demonstrated that the combination therapy resulted in significantly enhanced levels of DNA damage. Taken together, these data indicate that the combination of riluzole and radiotherapy has a therapeutic advantage over WBRT alone.

EXAMPLES

Example 1: Materials and Methods

Cell Lines hGRM1-expressing C8161 [wild type (wt) for RAS and BRAF] and UACC903 (wt for RAS, mutated B-RAF, V600E) human melanoma cell line and hGRM1-negative melanoma cell line UACC930 (wt for RAS, mutated B-RAF, V600E), were obtained from Dr. Mary J. C. Hendrix (Children's Memorial Research Center, Chicago, IL) and Dr. Jeffrey M. Trent (Translational Genomics Research Center, Phoenix, AZ), respectively. Cells were cultured in monolayer at 37° C. in a 5% CO2 humidified incubator, in RPMI (InVitrogen) supplemented with 10% fetal bovine serum (Sigma).

Clonogenic Survival Assays

Cells were trypsinized for retrieval and plated on 100-mm plates and allowed to attach overnight for 20 hours. Riluzole (25 mmol/L) was added at the 20-hour time point and allowed to incubate for 24 hours. Drug concentration (25 mmol/L) was chosen on the basis of a 96-well plate ATP luminescence cell viability assay with increasing concentrations of drug in irradiated. Cells were irradiated by a Gamma Cell 40 Exactor (MDS Nordion) irradiator and then incubated overnight (20 hours). Drug was aspirated and culture media replaced at 20 hours. Plates were then monitored for 10 to 21 days and stained with crystal violet for visual counting. Colonies which contained more than 50 cells were scored as clonogenic survivors.

MTT Cell Viability Assays

MTT cell viability/cell proliferation assays were performed with U87MG cells; the cells were either not treated (NT), treated with vehicle (Veh, DMSO) or riluzole at 5, 10, 25 or 50 µM for 7 days. Protein lysates were prepared from U87MG glioma cells that were either not treated (NT), treated with vehicle (Veh, DMSO), or riluzole at 10, 25 or 50 µM for 4 days, and subjected to Western immunoblots with antibody that recognizes both uncleaved and cleaved forms of poly (ADP-ribose) polymerase (PARP). U87MG xenograft mice, $10^6$ cells were injected subcutaneously into the dorsal flanks of each mouse. When the tumor volumes reached about 6-10 mm$^3$ the mice were divided into groups with similar tumor volume distribution and treatment was then initiated. The groups were no treatment (NT), vehicle (Veh, DMSO) and riluzole (10 mg/kg); treatment was administrated via oral gavage daily for 42 days. It was demonstrated that RIL-treated cells had higher levels of cleaved PARP on Western immunoblotting of cell lysates. These experiments were also repeated in U118MG and LN229 cell lines, with identical results.

MTT cell viability/cell proliferation assays were also performed with U118MG cells. As above, the cells were either not treated (NT), treated with vehicle (Veh, DMSO) or Riluzole at 5, 10, 25 or 50 µM for 7 days. U118MG xenograft mice, $10^6$ cells were injected subcutaneously into the dorsal flanks of each mouse, when the tumor volumes reach 6-10 mm$^3$ the mice were divided into groups with similar tumor volume distribution and treatment is then initiated. The groups were no treatment (NT), vehicle (Veh, DMSO) and Riluzole (10 mg/kg), treatment was administrated via oral gavage daily for 42 days.

Western Immunoblots

Western immunoblots of C8161 hGRM1-positive human melanoma cells either treated with riluzole for 24 hours or no treatment were conducted. Both sets of cells were irradiated at 2 or 4 Gy. Lysates were made at 24, 48, or 72 hours after irradiation. Protein lysates were prepared by washing cells with PBS, adding extraction buffer [50 mmol/L Tris, 150 mmol/L NaCl, 1 mmol/L EDTA (pH 8.0)], 1% NP40, 5% glycerol, 1 mmol/L Dithiothreitol, complete protease inhibitor cocktail (Roche), and phosphatase inhibitors I and II (Sigma). The samples were resolved in 10% gels (Bio-Rad), after which they were transferred onto nitrocellulose membranes. Membranes were blocked with 5% milk and 1% bovine serum albumin and then probed with antibodies against PARP and cleaved caspase-3. The same blot was probed with alpha-tubulin to show equal loading.

Cell Cycle Analysis

C8161 cells were plated at $0.5 \times 10^6$ per 100-mm culture plates and treated with either 8 Gy irradiation or with 25 mmol/L riluzole. After 24 hours, cells that had been treated with irradiation were exposed to riluzole at 25 mmol/L, and cells treated with riluzole were treated with 8 Gy irradiation. Cells were then collected at 48 hours and washed twice with PBS. Cell pellets were fixed by drop-wise addition of ice-cold 70% ethanol and incubated overnight at 4° C. Fixed cells were washed twice with ice-cold PBS and resuspended in 500 mL PBS. Cells were treated with 50 mL of RNase A solution (1 mg/mL; Sigma, R-4875) and labeled with 5 mL of propidium iodide (1 mg/mL; Sigma P4170) overnight. Cell cycle analysis was done within 24 hours by a Beckman Coulter system (FC 500 model). The experiment was repeated 3 times.

TABLE 2

Melanoma Cell Cycle Analysis of Riluzole Followed by Irradiation and Irradiation Followed by Riluzole

| | Riluzole followed by Radiation | | | | Radiation followed by Riluzole | | | |
|---|---|---|---|---|---|---|---|---|
| | Sub G1 | G1 | S | G2 | Sub G1 | G1 | S | G2 |
| Control (No treatment) | 14.15 | 33.53 | 22.55 | 29.74 | 12.09 | 35.21 | 23.59 | 28.95 |
| Riluzole (25 uM) | 3.59 | 16.25 | 18.45 | 61.64 | 24.91 | 29.13 | 22.86 | 22.86 |

Table 2. C8161 human melanoma cells were plated at $0.5 \times 10^6$ per 100-mm culture plates and treated with either 8 Gy irradiation or with 25 µM riluzole. After 48 hours, cells that had been treated with irradiation were exposed to riluzole at 25 uM, and cells treated with riluzole were treated with 8 Gy irradiation. The results displayed are the average of 3 experiments. Results were compared using students t-test, p=0.02 for No treatment versus riluzole in the group receiving riluzole before RT, and p=0.005 for pre-radiation riluzole compared to post-radiation.

Murine Xenograft Model hGRM-positive C8161 cells ($1 \times 10^6$) were injected into the flanks of 6-week-old nude mice (Taconic). When the tumors reached approximately 6 to 10 mm$^3$ the mice were randomly divided into 5 groups of 10 mice each: group 1 was left untreated (no treatment or NT), group 2 was treated twice with 4 Gy of irradiation only (IR), group 3 was treated with the dimethyl sulfoxide (DMSO) vehicle only (vehicle), group 4 was treated with 10 mg/kg of riluzole by oral gavage only (riluzole), and group 5 was first given 10 mg/kg of riluzole followed by 2 treatments of 4 Gy of irradiation. The irradiation was performed by the following protocol: at 24 hours post-riluzole or -vehicle administration, 2 mice at a time were placed in individual veterinarian-approved containers for use in the g-irradiator (Gammator 50, cesium 137 source; Radiation Machine Corp.). The mice were irradiated with a dose of 4 Gy, followed by a second dose of 4 Gy at 48 hours post-riluzole or -vehicle administration. At 24, 48, and 72 hours after the second dose of irradiation, mice in each group were sacrificed and tumor samples were removed. Half of the samples were snap-frozen for further molecular studies, and the other half was fixed in formalin for histologic analysis. The antibody to activated caspase-3 was utilized to visualize apoptotic cells. The average number of apoptotic cells per tumor was calculated by counting the apoptotic cells in 10 random highpowered fields.

The same xenograft experiment was performed, following the animals post irradiation and measuring the tumors with calipers twice per week. Oral riluzole was given each day by gavage to the groups receiving riluzole and radiation was delivered in 3 weekly fractions of 4 Gy to the groups receiving irradiation. The experiment was terminated after 25 days of treatment due to tumor burden in the NT and vehicle-treated animals.

The animals from the second xenograft experiment were sacrificed and half of the samples were snap-frozen for further molecular studies and the other half was dropped in formalin for histologic analysis. The antibody to gH2AX (Millipore) was utilized to visualize cells with DNA damage. The level of phosphorylated histone variant H2AX is a surrogate marker for levels of DNA damage. Immediately after double-strand breakage (DSB), gH2AX forms bright nuclear foci on immunofluorescent microscopy. The presence of gH2AX foci is widely regarded as a surrogate for and a sensitive marker of DSB in cells and have been shown to be specific for DSB.

Statistics

All clonogenic assays and cell cycle analyses experiments were repeated 3 times and the triplicate results are shown. Results of Western blots and xenograft experiments are from single experiments. Significance was determined by using unpaired Student's 2-tailed t test. A P value of ≤0.05 was considered significant.

Example 2: Examination of Peritumoral Glutamate Levels Before and After Concurrent RT and RIL Using Advanced MR Spectroscopy in Phase I Patients Paired pre- and post-therapy MR spectroscopy scans were obtained, evaluating glutamate levels in peritumoral edematous areas, allowing a non-invasive demonstration of the effect of the drug on the target. It is now understood that RIL treatment decreases the glutamate/creatine (Glu/Cr) ratio in paired, image-fused voxels within non-enhancing, T2/FLAIR regions of the MRI. This represents a novel and powerful in-vivo method to demonstrate an intracranial drug effect.

Example 3: Establishing a Primary Glioblastoma Xenograft Model in Zebrafish Using Cells Cultured from Primary Samples Obtained in Example 1

Glioblastoma exhibits genetic heterogeneity both within tumors and amongst patients. Thus it would be advantageous to add further therapeutic agents to the single-agent therapies, with or without RT, in order to achieve improvements in cure rates. Models that allow high throughput experimental drug testing offer the opportunity to identify novel compounds with anti-glioma activity. It is now understood that RT or the combination of RT/RIL induces specific "escape" responses in glioblastoma cells. The zebrafish model was utilized to identify additive/synergistic combination therapies with RT alone or RT/RIL and other candidate therapeutic agents.

Figure 1B:
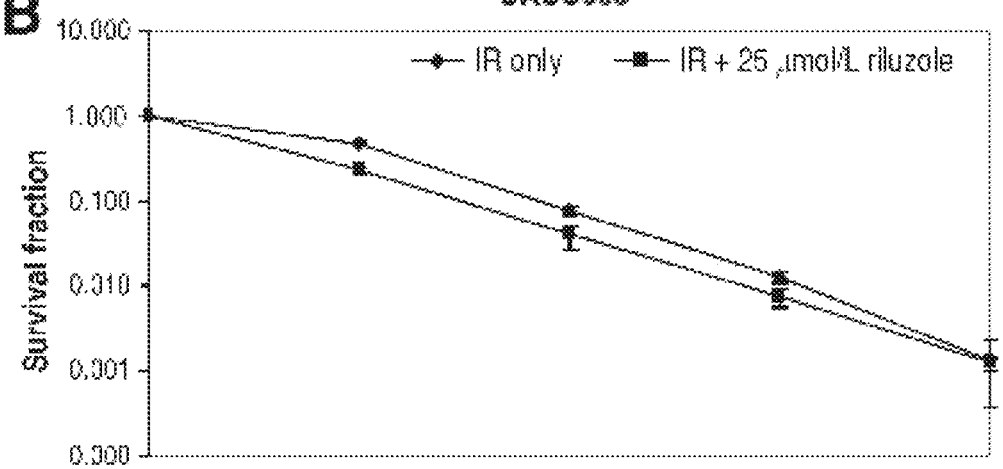
FIG. 1B shows survival fraction of hGRM1-positive UACC903 human melanoma cells treated with riluzole at 25 mmol/L for 24 hours followed by escalating doses of IR.
Figure 1C:
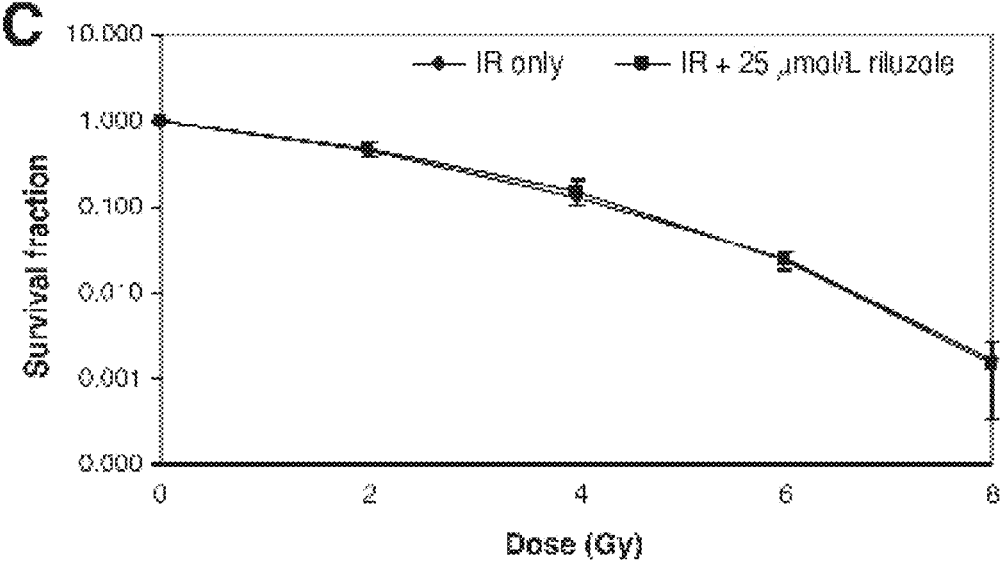
FIG. 1C shows survival fraction of hGRM1-negative UACC930 human melanoma cells treated with riluzole at 25 mmol/L for 24 hours followed by escalating doses of IR.

Example 4: Enhanced Radiosensitivity with Riluzole in hGRM1-Positive Human Melanoma Cell Lines Clonogenic assays were repeated 3 times and the triplicate results are aggregated in FIG. 1. In the hGRM1-positive cell line C8161, riluzole enhanced the lethal effects of ionizing radiation at the 2 and 4 Gy dose levels, with abrogation of the initial "shoulder" of the cell survival curve and a dose-modifying factor (DMF) of 1.48 [plating efficiency (PE)=12%]. The effect in FIG. 1 is statistically significant (P=0.048). Similarly, the UACC903 human melanoma cell line, also hGRM1-positive, showed enhanced cell death with riluzole when compared with ionizing radiation alone (FIG. 1; DMF=1.30, PE=19%). Clonogenic assays in hGRM1-negative human melanoma cell line, UACC930, revealed no difference in cell survival in experiments at 25 and 100 mmol/L of riluzole (PE=25%). This shows that riluzole likely has its radiation sensitizing effect on melanoma cells through inhibition of glutamergic signaling via hGRM1 receptor.

FIG. 1: Clonogenic assays. 1A, hGRM1-positive C8161 human melanoma cells were treated with riluzole at 25 mmol/L for 24 hours followed by escalating doses of ionizing radiation (IR). At 2 Gy, there was a 48% reduction (0.78±0.100 vs. 0.30±0.089, P=0.010) in cell survival in riluzole-treated cells versus nontreated cells. At 4 Gy, there was a 19% reduction (0.30±0.121 vs. 0.11±0.055, P=0.048) in cell survival in riluzole-treated cells versus nontreated cells. No differences were seen at 6 and 8 Gy. 1B, hGRM1-positive UACC903 human melanoma cells were treated with riluzole at 25 mmol/L for 24 hours followed by escalating doses of IR. At 2 Gy, surviving fraction (SF) 0.473±0.020 versus 0.233±0.056 (P=0.002). At 4 Gy, SF 0.078±0.010 versus 0.040±0.020 (P=0.046). At 6 Gy, SF 0.013±0.003 versus 0.008±0.003 (P=0.110). At 8 Gy, SF 0.001±0.001 versus 0.001±0.001 (P=0.930). 1C, hGRM1-negative UACC930 human melanoma cells were treated with riluzole at 25 mmol/L for 24 hours followed by escalating doses of IR. There was no difference between treated and untreated control UACC930 cells (P=NS).

Example 5: Apoptosis of hGRM1-Expressing Cells Exposed to Riluzole and Ionizing Radiation Cleaved forms of PARP and caspase-3 are common markers used for the assessment of apoptosis. Western blot analysis of irradiated C8161 cells with and without riluzole showed an increase in the cleaved form of PARP at 48 and 72 hours after irradiation. Riluzole treatment further augmented levels of cleaved PARP compared with irradiation alone. A second apoptosis marker, cleaved caspase-3 was also used to further confirm the increased in the number of apoptotic cells in riluzole plus ionizing radiation. Western blot analysis of irradiated C8161 cells with and without riluzole showed an increase in levels of cleaved caspase-3 at all time points: 0, 24, 48, and 72 hours after irradiation. Treatment with riluzole sensitized the cells to ionizing radiation in comparison with irradiation alone. Cells were either treated with IR at 2 Gy (2) or 4 GY (4) or not treated (0). Lysates were made immediately after IR or at 24 hours after IR and probed with anti-PARP and anticleaved PARP antibodies to assess apoptotic cells. The same blot was probed with a-tubulin to show equal loading.

Example 6: Combination Therapy with Riluzole and Irradiation Leads to G2/M Synchronization that is Sequence Dependent It was demonstrated that C816 cells that were treated with riluzole prior to irradiation showed a clear spike in the G2/M fraction, whereas cells treated in the reverse sequence showed no such effect. Table 2 displays the aggregate results from 3 experiments. Although not wishing to be bound by any theory, it is believed that G2/M synchronization is at least partially responsible for the enhanced radiosensitivity shown in these experiments. In a representative cell cycle analysis experiment from Table 2, the G2/M fraction was increased in C8161 cells when irradiation followed treatment with 25 mmol/L Riluzole.

In addition to these sequence experiments, cell cycle analysis was conducted after treatment of C8161 cells with the BAY 36-7620 compound, a noncompetitive GRM1 antagonist, showing no G2/M synchronization. This indicates that the effects of riluzole are mediated by mechanisms beyond those of just receptor blockade.

Figure 2:
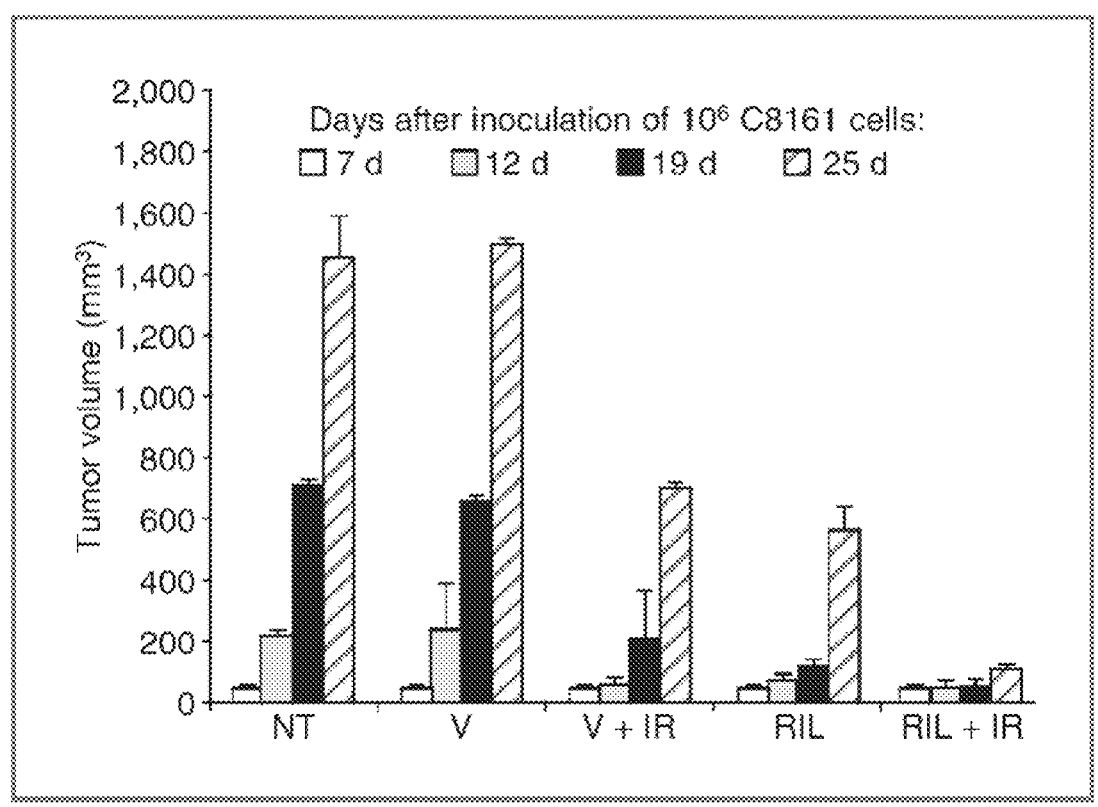
FIG. 2 displays tumor volume over time in a murine C8161 xenograft model. The treatment groups were: no treatment (NT), DMSO vehicle (V), V+irradiation (V+IR), riluzole (10 mg/kg; RIL), and riluzole (10 mg/kg) plus irradiation (RIL+IR).

Example 7: Effects of Ionizing Radiation and Riluzole in a Murine Xenograft Model It was demonstrated that in vitro cultured hGRM1-positive human melanoma cells were more sensitive to irradiation in the presence of riluzole. Xenograft experiments were then used to determine whether this observation could be shown in an in vivo animal system. A significant increase in the number of apoptotic tumor cells was observed by immunohistochemistry in the riluzole plus irradiation group than in the irradiation alone group or in control groups (P<0.001). There was also a significant difference in the number of apoptotic tumor cells in the riluzole plus irradiation tumors as compared with riluzole alone tumors at 24- and 48-hour time points (P<0.01; FIG. 2).

FIG. 2: Murine xenograft model. Immunodeficient nude mice were purchased from Taconic. C8161 cells were injected into flanks bilaterally at $10^6$ cells per site. Tumor size was measured twice a week with a vernier caliper. When tumor volumes reach 6 to 10 $mm^3$ the mice were randomly grouped into various treatments. Each treatment group consists of 10 mice. The groups were no treatment (NT), DMSO vehicle (V), V+irradiation (V+IR), riluzole (10 mg/kg; RIL), and riluzole (10 mg/kg) plus irradiation (RIL+IR). Oral riluzole was given each day by oral gavage. Irradiation was delivered in 3 weekly fractions of 4 Gy. The experiment was terminated after 25 days of treatment due to tumor burden in the NT and vehicle treated animals. There is at least an additive effect of the combination of riluzole and IR on the growth of these C8161-bearing xenografts.

In the second xenograft experiment, tumor volume was measured twice per week to determine whether riluzole could sensitize xenograft tumors to the effects of ionizing radiation and arrest or delay their growth. These results show that either riluzole or irradiation alone resulted in significantly smaller tumors at 19 and 25 days than untreated or vehicle treated control xenografts. However, the combination of riluzole and irradiation resulted in significantly smaller tumors as compared with untreated controls or to tumors treated with riluzole or irradiation alone at both 19 and 25 days. Xenograft harvests from this experiment revealed markedly enhanced DNA damage as measured by foci of gH2AX on immunohistochemistry.

Cleaved caspase-3 immunohistochemistry. Immunodeficient nude mice were purchased from Taconic. C8161 cells were injected into flanks bilaterally at $10^6$ cells per site. Tumor size was measured with a vernier caliper. When tumor volumes reached 6 to 10 $mm^3$ the mice were randomly grouped into various treatments. Each treatment group consisted of 10 mice. Group 1 was left untreated (no treatment), group 2 was treated twice with 4 Gy of ionizing radiation (IR) only (IR), group 3 was treated with the DMSO vehicle only (vehicle), group 4 was treated with 10 mg/kg of riluzole by oral gavage only (riluzole), and group 5 was first given 10 mg/kg of riluzole followed by 2 treatments of 4 Gy of irradiation (riluzole þ IR). The irradiation was performed by the following protocol: at 24 hours post-riluzole or -vehicle administration, 2 mice at a time were placed in individual veterinarian-approved containers for use in the g-irradiator (Gammator 50, cesium 137 source; Radiation Machine Corp). The mice were irradiated with a dose of 4 Gy, followed by a second dose of 4 Gy at 48 hours post-riluzole or -vehicle administration. At 24, 48, and 72 hours after the second dose of irradiation, mice in each group were sacrificed and tumor samples were removed. Half of the samples were snap-frozen for further molecular studies, and the other half was fixed in formalin for histologic analysis. The antibody to activated caspase-3 was utilized to visualize apoptotic cells. A significant difference was observed in the number of apoptotic tumor cells in the riluzole plus irradiation group than in the irradiation alone group or the control groups ($P<0.001$). There was also a significant difference in the number of apoptotic tumor cells in the riluzole plus irradiation tumors as compared with the riluzole alone tumors at 24- and 48-hour time points ($P<0.01$).

H2AX immunohistochemistry. C8161 xenografts were treated with riluzole when the tumors were 6 $mm^3$ and the mice were treated with ionizing radiation (4 Gy; IR) once a week for 3 weeks as described in FIG. 2. Riluzole was given for 3 continuous weeks. The number of H2AX-positive cells was calculated from counting of 10 random fields.

U87MG-Luc xenograft mice, $10^6$ cells were injected subcutaneously into the dorsal flanks of each mouse, when the tumor volumes reach 6-10 $mm^3$ as measured by vernier caliper the mice were randomized into groups with similar tumor volume distribution and treatment is then initiated. The groups are no treatment (NT), vehicle (Veh, DMSO) and Riluzole (10 mg/kg), treatment was administrated via oral gavage daily for 37 days. *, $p<0.05$, comparison of Riluzole treated mice with vehicle treated ones. Quantitation of the bioluminescence signal intensities from images acquired by IVIS small animal imaging system shown in panels C and D. Luciferen (30 mg/ml) stock solution was used and each animal received intraperotoneal injection of luciferen (6 mg/mouse) at least 20-30 min prior to acquisition of images. The data were expressed as photon flux (photons/s/cm2/steradian), where steradian refers to the photons emitted. The background photon flux was subtracted from the signal intensities measured at the same site. Data were normalized to peak signal intensity of each time course and expressed as mean values with standard deviations. **, $p<0.06$, comparison of Riluzole treated mice with vehicle treated ones.

Figure 3A:
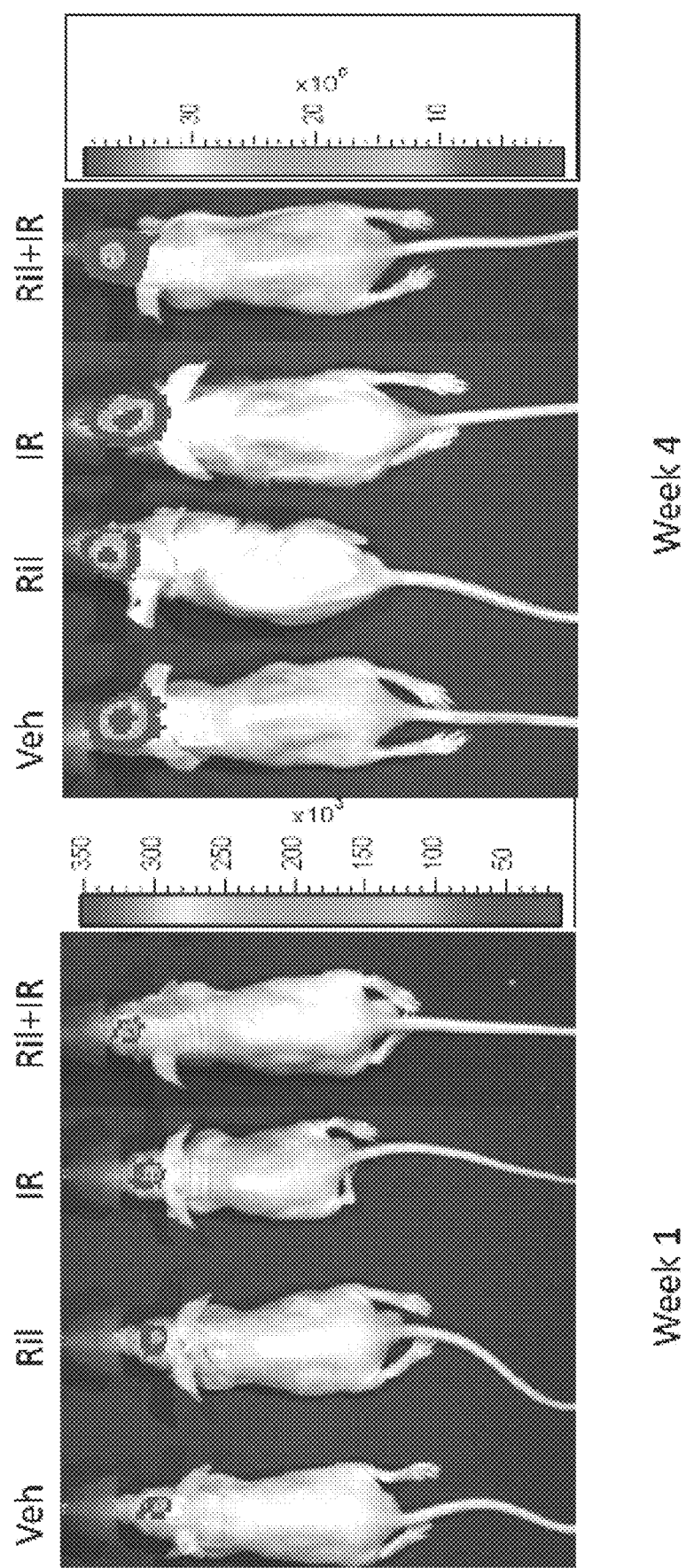
FIG. 3A shows initial and terminal images of select mice with intracranial orthotopic transplants of C8161-luc+human melanoma cells, treated with DMSO (Veh), riluzole (10 mg/kg), ionizing radiation (4 Gy) or a combination of the two.
Figure 3B:
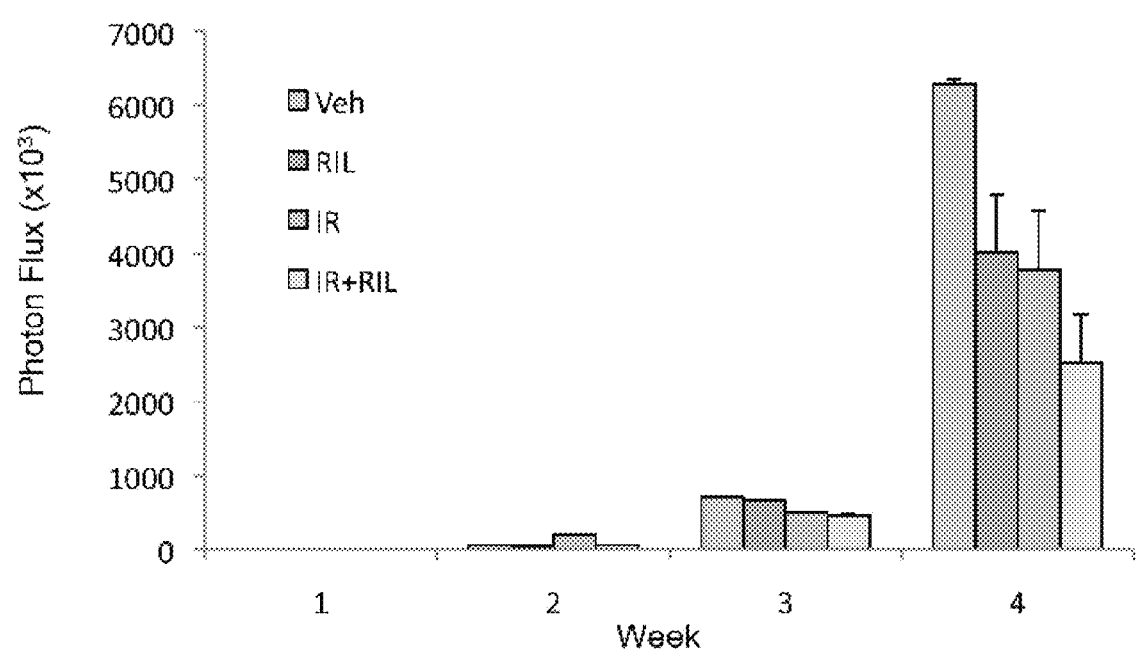
FIG. 3B displays the photon flux over time.

Example 8: Combination of Riluzole and IR Reduces Human Melanoma Cell Growth in Orthotopic Model of Brain Metastasis The brain is a common site of metastasis for patients with various neoplasias including melanoma, breast cancer, lung cancer, and colorectal cancer. Despite maximally tolerated doses of radiation to the whole brain, patients with multiple brain metastases from solid tumors often show progression in the brain contributing to neurological deterioration, decreased quality of life, and poor survival. It was demonstrated that in vitro cultured GRM1-positive human melanoma cells were more sensitive to irradiation in the presence of riluzole. To mimic brain metastases observed in melanoma patients, brain metastases in an animal model C8161-luc cells were introduced into the brains of nude mice by intracranial injection and monitored for tumor establishment using luminescent imaging. Once luminescent signal was detected, animals were separated into groups and treated with either DMSO (Veh), riluzole (10 mg/kg), ionizing radiation (4 Gy) or a combination of the two. Animals were terminated after 3 weeks of treatment. Images of select animals showing initial and terminal images are shown in FIG. 3A. FIG. 3B shows the intensities of the quantified emitted signals. The data were expressed as photon flux (photons/s/$cm^2$/steradian, where steradian refers to the photons emitted). The background photon flux was subtracted from the signal intensities measured at the same site. Data were normalized to peak signal intensity of each time course. Upon initial detection animals were imaged weekly to determine if riluzole could further sensitize orthotopic tumors to the effects of IR.

The results of the intracranial model show that riluzole and irradiation alone resulted in decreased luminescence compared to vehicle treated alone (FIG. 3A). The combination of riluzole and irradiation resulted in much less tumor cell growth as indicated by luminescent signal detected and quantified.

Riluzole Causes DNA Damage in Apoptosis-Deficient Cells

To understand whether riluzole induces DNA damage separate from any apoptotic effect, immortalized baby mouse kidney epithelial cells (D3) were used; these cells are deficient in apoptosis through deletion of BAX and BAK. Either mGRM1 or an empty vector was introduced into D3 cells, which were treated with etoposide (control for DNA damage) or riluzole for various time points up to 24 hours. These treated cells were stained with γ-H2AX and 53BP1, both known to localize at sites of DNA double stranded breaks. It was demonstrated that both D3-vec and D3-mGRM1 cells displayed induction and co-localization of 53BP1 and γ-H2AX foci after etoposide treatment. In contrast, only D3-mGRM1 cells (but not vector controls) displayed induction of clear nuclear 53BP1 and γ-H2AX foci after riluzole treatment, again consistent with the induction of DNA breaks in this setting. These results indicate that, even in the absence of apoptosis, riluzole-mediated DNA damage occurs in cells with ectopic glutamate signaling and is consistent with the understanding that riluzole alters levels of intracellular reactive oxygen species (ROS) by depleting intracellular cysteine and glutathione in vitro, likely mediated by an effect on system $X^c$.

Stable empty vector control (D3-vec) and mGRM1 apoptosis defective immortalized baby mouse kidney epithelial clones (D3-mGRM1) were treated with riluzole for 3 hrs followed by immunofluorescence stains with DAPI, 53BP1 or γ-H2AX.

RIL Mediated DNA Damage in Glioma Cells

Levels of ROS in cells treated with RIL or vehicle were evaluated, and increased ROS was demonstrated. Furthermore, γ-H2AX levels were demonstrated in RIL treated cells by Western blotting, and co-localization of 53BP1 or γ-H2AX after RIL treatment.

LN229 and U87MG cells were treated with vehicle (DMSO) or 10 uM riluzole for various time periods. The cells were incubated with 2',7'-dichlorodihydrofluorescein diacetate (Sigma) for 20 min at 37 deg. ROS-mediated oxidation of fluorochrome fluorescence was measured with flow cytometer, showing enhanced ROS with RIL Western blots for γ-H2AX were prepared for cell lysates treated with either no treatment (NT), vehicle (DMSO), etoposide (positive control) or riluzole. RIL treatment caused DNA damage. Co-localization was demonstrated after both etoposide (ET) and RIL treatment, using immunofluorescence stains for DAPI, γ-H2AX, 53BP1 or merged.

Example 9: Phase I Trial of Concurrent RT and Riluzole (RIL) in Patients with MGMT-Expressing Glioblastomas MGMT-expressing tumors are less likely to benefit from concurrent temozolamide therapy during RT, and the prognosis remains exceptionally poor in this group of patients. A phase I study was designed with correlative endpoints, including patients with MGMT-active glioblastomas. All patients received standard RT with temozolamide for 30 fractions (60 Gy); patients also received escalating doses of concurrent RIL during the RT. A standard 3+3 design with 3 dose levels was utilized. All patients were consented (when possible) for pre-therapy specimen retrieval for correlative analyses. Patients with disease progression supplied biopsy confirmation and specimen retrieval, creating paired initial and recurrent specimens A standard 3+3 design with a total of 3 dose levels was utilized (3-6 patients per dose cohort based on incidence of predefined dose-limiting toxicities, Table 1).

TABLE 1

| Dose level | Dose of Riluzole |
| --- | --- |
| −1 | 50 mg daily |
| 0—Starting Dose | 50 mg twice daily (100 mg daily) |
| 1 | 100 mg in the AM and 50 mg in the PM (150 mg daily) |
| 2 | 100 mg twice daily (200 mg daily) |

The Maximum Tolerated Dose (MTD) is defined as follows: with starting dose level I, groups of 3 patients are entered at a dose level:
  If none of 3 patients treated at a dose level experience dose limiting toxicity (DLT), then the dose is escalated to the next dose level.
  If ⅓ patients have DLT, then 3 more patients are treated at this dose level.
    If none of these additional patients has DLT, the dose is escalated;
    If only one of these additional patients has DLT, the current dose level is declared as MTD;
    If all of these additional patients have DLT, then
      If the current dose level is not level 0, three more patients are treated at the previous dose level if no more than 3 patients had been treated at that dose level; otherwise previous dose level is declared as MTD;
      If the current dose level is level 0, three patients are treated at dose level −1. Treat three additional patients in dose level −1 if only 1 patient has DLT.
  If at least ⅔ patients have DLT, then
    If the current dose level is not level 0, three more patients are treated at the previous dose level if no more than 3 patients had been treated at that dose level; otherwise previous dose level is declared as MTD;
    If the current dose level is level 0, three patients are treated at dose level −1. Treat three additional patients in level −1 if only 1 patient has DLT.

The MTD is the dose level where no more than ⅖ patients experience DLT and at least ⅔ or ⅗ patients treated with the next higher dose level have experienced DLT.

It is now understood that tumors with higher baseline expression of mGluR3/GRM3 are associated with improved survival in patients treated with RIL. Again, the overexpression of system $X^c$ increases intracellular glutathione and increases extracellular glutamate which then acts as a paracrine/autocrine growth and motility factor for glioma progression through stimulation of mGluR3. It is also now understood that RIL disrupts this axis. Therefore, all patients are consented for pre-therapy specimen retrieval for correlative analyses and to establish cell cultures for in vitro work from primary specimens. Specimens are immediately placed in OTC for routine histology and immunohistochemistry (IHC) and, (when possible) a second sample is preserved in liquid nitrogen for Western Blotting and RT-PCR analysis. Baseline expression of GRM3 was specifically examined due to the significant evidence supporting its role in glioma progression; however, the entire panel of ionotropic and metabotropic glutamate receptors as well as xCT was also examined. Importantly, patients with disease progression have biopsy confirmation and specimen retrieval, creating paired initial and recurrent specimens. This allows examination and comparison of glutamate receptor expression at progression, and exploration of other known survival pathways operant in glioblastomas.

Pre- and post-therapy MR spectroscopy (MRS) were employed to identify changes in glutamate levels in regions of peri-tumoral edema after treatment with riluzole. To demonstrate this effect in vivo, pre- and post-therapy MR spectroscopy was utilized to examine the glutamate to creatine (Glu/Cre) ratio in voxels representing peri-tumoral edema.

MR spectroscopy (MRS) is an established clinical method to measure metabolites such as choline, lactate, and N-acetyl aspartate (NAA) in the brain. The creatine (Cre) concentration is relatively stable and is often used as a reference metabolite and internal control. Patients in the phase I trial (Example 1) have MRS scans 1-14 days before and after starting and ending (respectively) their concurrent cranial RT/TMZ+RIL. A 3T MR unit was employed, with acquisition parameters and analysis techniques that are similar to those used in clinical diagnostic MRS. Pre- and post-therapy biopsies are not feasible in the brain; a non-invasive method to demonstrate the effect of drug on target is both powerful and adaptable to clinical use. Fused pre- and post-scans were created to confirm that paired voxels of interest are in identical anatomical regions. Thus, it has now been demonstrated that RIL treatment decreases the glutamate/creatine (Glu/Cre) ratio in paired, image-fused voxels within non-enhancing, T2/FLAIR regions of the MRI.

Non-linear dimensionality reduction and classifier ensemble schemes for (a) integrating MRS and MM signatures for prostate cancer detection, and also for (b) discriminating high versus low Gleason grade prostate cancer, can be leveraged to identify imaging marker changes pre-, and post-therapy. This allows one to correlate clinical and pathological factors, including expression of surface glutamate receptors and xCT, with response on MRS imaging.

Example 10: Zebrafish Xenograft Model

Primary glioblastoma cells were used to study the mechanistic basis for enhanced DNA damage with RIL and to identify additive/synergistic combination therapies of RT or RT/RIL and other candidate therapeutic agents in a zebrafish xenograft model. Without wishing to be bound by any theory, it is believed that RIL treatment results in reduced extracellular release of glutamate and impairs cystine-glutamate exchange by system $X^c$. This in turn causes depleted levels of intracellular GSH and enhances ROS mediated RT-induced DNA damage and cell death. Thus tumor cells can be rescued by pharmacological GSH mimetics. This was demonstrated in vitro with primary samples with established glioma cell lines. Briefly, tumor specimens are received from the operating room into DMEM/F12 with 1× antibiotic, 20 ng/mL EGF, 20 ng/mL FGF, 1×B-27 supplement or PBS. The specimens were transferred to a petri dish and rinsed in HBSS. Gentle mechanical dissociation of the tumor was performed by using sterile scalpels and forceps; single-cell suspensions were created using a needle syringe and this suspension was passed through a 40-μm cell strainer to remove nonhomogenized tissues. Cells were cultured in nonadherent plates or culture flasks. Neurospheres were sorted by flow cytometry to select the CD133+ TIC population.

Levels of extra-cellular glutamate were determined in three glioma cell lines, U87MG, LN229 and U118MG for 4 days; C8161 melanoma cells were used as positive control, media only with no cells was used as negative control.

The testing protocol includes:
1. Conducting sequence and time-based clonogenic assays to define the optimal parameters for enhanced radiosensitivity with RIL.
2. Examining DNA repair kinetics in vitro glioma cell lines by quantifying Western immunoblots and immunofluorescent foci of γH2AX after irradiation in RIL treated and untreated groups over a range of time periods after RT. H2AX is a histone variant and its phosphorylated form is designated γH2AX. Immediately after DNA double strand breaks (DSB), γH2AX forms bright nuclear foci on immunofluorescent microscopy. In Western immunoblots, etoposide-treated cells were utilized as positive controls for the appearance of γH2AX. These experiments allow for an assessment as to whether enhanced DNA damage is a result of an increase in absolute number of DSBs (as would be the case with ROS enhancement) or slower/inadequate DNA repair kinetics in RIL treated cells (which would point to downstream effects of RIL on the DNA repair axis). In addition, levels of RAD51 foci as a specific assay for homologous repair, and levels of Ku80 as a marker of non-homologous, end-joining (NHEJ) repair, were assessed.
3. Analyzing intracellular GSH and ROS levels with and without RIL. A commercially available glutathione assay kit (Cayman Chemical) is used on RIL treated and untreated cells and is correlated with the level of γH2AX expression and activated caspace-3 levels. Similarly, intracellular ROS levels are measured in vitro in treated and untreated cells loaded with 15 μM DHR123 (Sigma) followed immediately by flow cytometry. Positive controls are treated with 0.25 mM $H_2O_2$ for 4 hours; cells are read within one hour of administering the dye. It is now understood that RIL treated cells are rescued in vitro and in vivo from enhanced DNA damage by well-known radical scavengers such as Vitamin E and thymopetin. RIL effects on RT-induced DNA damage in vitro and in vivo were compared with well-studied metabotropic and ionotropic glutamate receptor inhibitors, and with specific system $X^c$ inhibition to establish a mechanistic rationale for the use of RIL.

These experiments have been performed in commercially available glioblastoma cell lines.

The CD133+ TICs were specifically studied. Glioblastoma exhibits genetic heterogeneity both within tumors and amongst patients. Thus it would be advantageous to add further therapeutic agents to the single-agent therapies, with or without RT, in order to achieve improvements in cure rates. Models that allow high throughput experimental drug testing offer the opportunity to identify novel compounds with anti-glioma activity. The advantages of a zebrafish xenograft model include optical clarity allowing for in vivo monitoring of tumor initiation, and the ability to test several compounds applied directly in the water. CD133+ glioma tumor initiating stem cells (TICs) from primary glioblastoma specimens after dissociation were selected, cultured as tumor cubes, and the CD133+ cells sorted. CD133+ TICs have been implicated in radioresistance, better repair of sublethal DNA damage, and hypoxic resistance. TICs were marked with quantum dots to allow cell tracking in vivo and microinjected into the brain of preimmune fish embryos. The resulting zebrafish with tumor xenografts were subjected to 10 Gy RT, RIL, or the combination to study anti-xenograft activity; apoptosis and DNA damage was assessed in tumor xenografts as described above. Uniquely, it has been demonstrated that zebrafish can tolerate 25 Gy as a sublethal total body dose. This surprising fact makes the zebrafish a particularly valuable model to study RT effects on xeno-transplanted tumors, even with a 10 Gy dose. In addition to this, it has also been demonstrated that the direct intracranial microinjection of tumor cells in zebrafish is feasible.

The foregoing examples demonstrate that the addition of riluzole (RIL) treatment to radiation therapy (RT) enhances clonogenic cell kill and increases apoptotic markers in melanoma cells in vitro, increases apoptosis in mouse melanoma xenografts, results in significant growth delay in a mouse xenograft model, and increases DNA damage in a mouse xenograft. These results are applicable to any metastatic disease, as well as being relevant to other cancerous tumors, including gliomas.

It is understood that the specific embodiments of the invention disclosed herein are not to be construed to limit the present invention in any way, and that other embodiments which might occur to one skilled in the art, fall within the scope of the present invention.

All references cited herein are incorporated herein in their entireties.

The invention claimed is:

1. A method of treating a tumor in a patient in need thereof, said tumor comprising cells expressing a metabotropic glutamate receptor, said method comprising:
   (a) initially administering riluzole to said patient within the time window of about 24 to about 48 hours before radiation treatment,
   (b) optionally, ceasing riluzole administration, and
   (c) at least 24 hours following the initial treatment with riluzole, irradiating the tumor cells with a therapeutically effective dose of ionizing radiation, wherein said metabotropic glutamate receptor is metabotropic glutamate receptor 1 (mGluR1; GRM1).

2. The method of claim 1, wherein the dose of ionizing radiation is reduced compared to the dose of ionizing radiation prescribed for tumors that are not administered riluzole.

3. The method of claim 1, wherein the tumor is a melanoma tumor.

4. The method of claim 3, wherein the melanoma tumor is a metastatic tumor.

5. The method of claim 4, wherein the metastatic tumor is a cerebral metastatic tumor.

6. The method of claim 5, wherein said ionizing radiation comprises whole-brain irradiation.

7. The method of claim 6, wherein the dose of ionizing radiation is reduced compared to the dose of ionizing radiation prescribed for tumors that are not administered riluzole.

8. The method of claim 5, wherein the ionizing radiation comprises fractionated whole-brain irradiation.

9. The method of claim 8, wherein the size of the section irradiated is reduced compared to the size of irradiated sections irradiated in tumors that are not administered riluzole.

10. The method of claim 1, wherein riluzole administration begins about 36 to about 48 hours prior to radiation treatment.

11. The method of claim 1, wherein the last dose of riluzole before radiation treatment is administered at least 24 hours before radiation treatment.

12. The method of claim 1, wherein riluzole administration continues until initiation of radiation treatment, or throughout radiation treatment.

13. The method of claim 1, wherein riluzole administration continues post-radiation treatment at the same or a lower amount.

14. The method of claim 1, further comprising administering to said patient one or more additional therapeutic agents in an amount effective to kill said tumor cells when used in combination with riluzole and ionizing radiation.

15. A method of treating a melanoma tumor in a patient in need thereof, said melanoma tumor comprising cells expressing metabotropic glutamate receptor 1 (mGluR1; GRM1), said method comprising:
   (a) initially administering riluzole to said patient within the time window of about 24 to about 48 hours before radiation treatment, thereby increasing the population of tumor cells sensitive to ionizing radiation; followed by
   (b) optionally, ceasing riluzole administration; and
   (c) at least 24 hours following the initial treatment with riluzole, irradiating the tumor cells with ionizing radiation so that the growth of said tumor cells is reduced, thereby resulting in reduced melanoma tumor growth in said patient.

16. The method of claim 15, wherein the dose of ionizing radiation is reduced compared to the dose of ionizing radiation prescribed for tumors that are not administered riluzole.

17. The method of claim 15, wherein the melanoma tumor is a metastatic tumor.

18. The method of claim 17, wherein the metastatic tumor is a cerebral metastatic tumor.

19. The method of claim 18, wherein said ionizing radiation comprises whole-brain irradiation.

20. The method of claim 19, wherein the dose of ionizing radiation is reduced compared to the dose of ionizing radiation prescribed for tumors that are not administered riluzole.

21. The method of claim 18, wherein the ionizing radiation comprises fractionated whole-brain irradiation.

22. The method of claim 21, wherein the section irradiated is reduced compared to the size of the section irradiated for tumors that are not administered riluzole.

23. The method of claim 15, wherein riluzole administration begins about 36 to about 48 hours prior to radiation treatment.

24. The method of claim 15, wherein the last dose of riluzole is administered at least 24 hours before radiation treatment.

25. The method of claim 15, further comprising administering to said patient one or more additional therapeutic agents in an amount effective to kill said tumor cells when used in combination with said riluzole and said ionizing radiation.

* * * * *